US010588945B2

(12) United States Patent
Tanino et al.

(10) Patent No.: US 10,588,945 B2
(45) Date of Patent: Mar. 17, 2020

(54) AGENT FOR PREVENTING ONSET OF IDIOPATHIC OSTEONECROSIS OF FEMORAL HEAD AND/OR SUPPRESSING PROGRESS OF SAME

(71) Applicants: ASAHI KASEI PHARMA CORPORATION, Tokyo (JP); NATIONAL UNIVERSITY CORPORATION ASAHIKAWA MEDICAL UNIVERSITY, Asahikawa-shi, Hokkaido (JP)

(72) Inventors: Hiromasa Tanino, Asahikawa (JP); Hiroshi Ito, Asahikawa (JP)

(73) Assignees: ASAHI KASEI PHARMA CORPORATION, Tokyo (JP); NATIONAL UNIVERSITY CORPORATION ASAHIKAWA MEDICAL UNIVERSITY, Asahikawa-Shi (JP)

( * ) Notice: Subject to any disclaimer, the term of this patent is extended or adjusted under 35 U.S.C. 154(b) by 0 days.

(21) Appl. No.: 15/739,838

(22) PCT Filed: Jul. 4, 2016

(86) PCT No.: PCT/JP2016/069779
§ 371 (c)(1),
(2) Date: Dec. 26, 2017

(87) PCT Pub. No.: WO2017/006908
PCT Pub. Date: Jan. 12, 2017

(65) Prior Publication Data
US 2018/0185454 A1 Jul. 5, 2018

(30) Foreign Application Priority Data
Jul. 7, 2015 (JP) ................. 2015-136533

(51) Int. Cl.
*A61K 38/29* (2006.01)
*A61P 19/06* (2006.01)
*A61K 9/19* (2006.01)
*A61P 19/08* (2006.01)
*A61K 9/00* (2006.01)

(52) U.S. Cl.
CPC ............ *A61K 38/29* (2013.01); *A61K 9/0019* (2013.01); *A61K 9/19* (2013.01); *A61P 19/08* (2018.01)

(58) Field of Classification Search
None
See application file for complete search history.

(56) References Cited

FOREIGN PATENT DOCUMENTS

JP 2012-136478 A 7/2012

OTHER PUBLICATIONS

Arai et al., "The study on the suppressing effect of teriparatide on the progression of collapse of the epiphysis in idiopathic osteonecrosis of the femoral head", Hokkaido Journal of Orthopaedics and Traumatology, 2013, vol. 125, p. 83, 2-I-2-2. (with English translation).*
Arai et al., "The study on the suppressing effect of teriparatide on the progression of collapse of the epiphysis in idiopathic osteonecrosis of the femoral head", Hip Joint, Aug. 25, 2014, vol. 40, p. 14-17. (with English translation).*
Nakano, T., "Once-weekly teriparatide treatment on osteoporosis", Clinical Calcium, Dec. 28, 2013, vol. 24(1), p. 100-105. (with English translation).*
Arai et al., "The study on the suppressing effect of teriparatide on the progression of collapse of the epiphysis in indiopathic osteonecrosis of the femoral head," Hip Joint (Aug. 25, 2014), vol. 40, pp. 14-17, with English translation.
Argarwala et al., "Ten-Year Follow-Up of Avascular Necrosis of Femoral Head Treated with Alendronate for 3 Years," The Journal of Arthroplasty (2011), vol. 26, No. 7, pp. 1128-1134.
Bashutski et al., "Teriparatide and Osseous Regeneration in the Oral Cavity," N. Engl. J. Med. (2010), vol. 363, pp. 2396-2405.
Chen et al., "Alendronate in the Prevention of Collapse of the Femoral Head in Nontraumatic Osteonecrosis," Arthritis & Rheumatism (May 2012), vol. 64, No. 5, pp. 1572-1578.
Cheung, A. and E. Seeman, "Teriparatide Therapy for Alendronate-Associated Osteonecrosis of the Jaw," N. Engl. J. Med. (Dec. 16, 2010), vol. 363, No. 25, pp. 2473-2474.
Dayisoylu et al., "The effects of adjuncitve parathyroid hormone injection on bisphosphonate-related osteonecrosis of the jaws: an animal study," Int. J. Oral. Maxillofac. Surg. (2013), vol. 42, pp. 1475-1480.
Fabbriciani et al., "Transient osteoporosis of the hip: a successful treatment with teriparatide," Rheumatol. Int. (2012), vol. 31, pp. 1367-1370.
Fukuda et al., "Weekly Teriparatide for Delayed Unions of Atypical Subtrochanteric Femur Fractures," Biol. Ther. (2014), vol. 4, pp. 73-79.
International Search Report dated Aug. 30, 2016, in PCT International Application No. PCT/JP2016/069779.
Ito et al., "Biploar Hemiarthroplasty for Osteonecrosis of the Femoral Head," Clinical Orthopaedics and Related Research (May 2000), No. 374, pp. 201-211.
Ito et al., "Long-term results of conventions varus half-wedge proximal femoral osteotomy for the treatment of osteonecrosis of the femoral head," J. Bone Joint Surg. Br. (2012), vol. 94-B, pp. 308-314.
Kubo, "Definition, classification, and pathological characteristics of idiopathic osteonecrosis of the femoral head," N. Sugano (Ed.), Kinpodo (2010), pp. 3, 18, with partial English translation.

(Continued)

*Primary Examiner* — Xiaozhen Xie
(74) *Attorney, Agent, or Firm* — Birch, Stewart, Kolasch & Birch, LLP (57) ABSTRACT

[Problem] To provide an agent for preventing the onset of idiopathic osteonecrosis of the femoral head and/or suppressing the progress of the same. [Solution] An agent for preventing the onset of idiopathic osteonecrosis of the femoral head and/or suppressing the progress of the same comprising parathyroid hormone or a derivative thereof as an active ingredient, characterized by being administered intermittently.

9 Claims, 2 Drawing Sheets

(56) References Cited

OTHER PUBLICATIONS

Lai et al., "The Use of Alendronate to Prevent Early Collapse of the Femoral Head in Patients with Nontraumatic Osteonecrosis," The Journal of Bone and Joint Surgery (Oct. 2005), vol. 87-A, No. 10, pp. 2155-2157.

Manabe et al., "Human parathyroid hormone (1-34) accelerates natural fracture healing process in the femoral osteotomy model of cynomolgus monkeys," Bone (2007), vol. 40, pp. 1475-1482.

McKenna, M. J., "Bilateral avascular necrosis of the femoral head and teriparatide: Consequence or coincidence," Bone (2008), vol. 42, p. S80, Article 138.

Nakano, "Shu 1 Kai Teriparatide Hika Chusha . . . " Clinical Calcium (Dec. 28, 2013), vol. 24, No. 1, pp. 100-105, with English translation.

Neuprez et al., "Teriparatide Therapy for Denosumab-Induced Osteonecrosis of the Jaw in a Male Osteoporotic Patient," Calcif. Tissue Int. (2014), vol. 95, pp. 94-96.

Nishii et al., "Does Alendronate Prevent Collapse in Osteonecrosis of the Femoral Head?" Clinical Orthopaedics and Related Research (Feb. 2006), No. 443, pp. 273-279.

Ohkawa et al., "Intermittent administration of human parathyroid hormone (1-34) increases new bone formation on the interface of hydroxyapatite-coated titanium rods implanted into ovariectomized rat femora," J. Orthrop. Sci. (2008) vol. 13, pp. 553-542.

Okimoto et al., "Effect of week one time intermittent administration and withdrawal of human parathyroid hormone (1-34) on dynamic strength of cortical bone of . . . ," The Japanese Society for Bone and Mineral Research Zasshi (1998), vol. 15, No. 4, pp. 177-181, with English translation.

Sugano et al., "Diagnostic criteria for non-traumatic ostonecrosis of the femoral head," J. Bone Joint Surg. [Br] (1999), vol. 81-B, pp. 590-595.

Sugano et al., "Prognostication of Osteonecrosis of the Femoral Head in Patients with Systemic Lupus Erythematosus by Magnetic Resonance Imaging," Clinical Orthopaedics and Related Research (Aug. 1994), No. 305, pp. 190-199.

\* cited by examiner

Figure 2

AGENT FOR PREVENTING ONSET OF IDIOPATHIC OSTEONECROSIS OF FEMORAL HEAD AND/OR SUPPRESSING PROGRESS OF SAME

TECHNICAL FIELD

The present invention relates to an agent for preventing the onset of idiopathic osteonecrosis of the femoral head and/or suppressing the progress of the same.

BACKGROUND ART

Idiopathic osteonecrosis of the femoral head (ION) is an intractable disease of unknown etiology, associated with steroid administration and excessive alcohol intake, in which part of the femoral head necroses. There are said to be approximately 2200 new cases of ION countrywide yearly (Non-patent Reference 1). Peak onset occurs in relatively young people in their 30s to 40s. If the femoral head collapses, it causes severe pain and ADL restrictions, necessitating surgical treatment such as osteotomy and artificial hip joint replacement. The results of surgical treatment of ION have been extensively researched (Non-patent References 2 and 3), but there is few research on conservative treatments.

Fragility fractures based on osteoporosis have become a problem in recent years, and a variety of osteoporosis therapeutics are being developed. Bisphosphonates among them play a central role and actualize their effect by suppressing bone resorption by lowering the activity of osteoclasts. Administration of bisphosphonates as a conservative treatment of ION is reported to decrease the rate of femoral head collapse after ION onset (Non-patent References 4-7).

Parathyroid hormone (PTH) has the kidneys and bones as its main target organs and is a hormone that acts to raise the blood Ca concentration. Persistent elevation of PTH activity causes bone loss. However, intermittent administration of PTH is said to have the effect of increasing bone mass and preventing bone fractures, and intermittently administered PTH formulations have become available for use as osteoporosis therapeutics in recent years. These PTH formulations have a bone formation promoting action not seen with conventional osteoporosis therapeutics and are expected to serve as more potent osteoporosis therapeutics. PTH formulations have been approved as osteoporosis therapeutics, but efficacy has also been reported recently in the treatment of osteonecrosis of the jawbone and bone formation after periodontal surgery (Non-patent References 8 and 9). Animal studies suggest utility in bone formation surrounding implants and promotion of the healing of bone fractures (Non-patent References 10 and 11). The possibility of promoting the treatment of transient osteoporosis of the hip in the hip joint is also suggested (Non-patent Reference 12).

Experimental results on the suppressive effect on femoral head collapse have also been reported in ION, focusing on the bone formation promoting action of teriparatide (Non-patent Reference 15). This report took the difference in femoral head collapse values before and after administration using simple x-ray frontal views as the endpoint; the extent of suppression of progress of the stage was not evaluated. Furthermore, this report is a trial results report using alendronate as the control; the existence of a placebo control is unclear. The method of assigning teriparatide and alendronate is also unclear. In addition, this report does not disclose the dosage and administration of teriparatide. It is stated that teriparatide tended to suppress femoral head collapse progress in comparison to alendronate as the result, but no statistical superiority between the two groups was found.

Furthermore, the bone density and clinical course of 40 subjects administered 20 µg/day of teriparatide were also reported. Ten of them (25%) had a decrease in femoral bone density, and one is introduced as a case in which bilateral osteonecrosis of the femoral head developed, although the relationship to the drug is unclear (Non-patent Reference 16).

Moreover, teriparatide administration is reported to have an effect against osteonecrosis of the jawbone induced by bisphosphonates and denosumab (Non-patent References 17 and 18), but this report discloses nothing whatsoever about the effect of teriparatide on ION.

PRIOR ART REFERENCES

Non-Patent References

Non-patent Reference 1: Idiopathic osteonecrosis of the femoral head, S. Kubo, N. Kanno (editor), Kinpodo, 2010
Non-patent Reference 2: J Bone Joint Surg Br 94 (3), 308-14, 2012
Non-patent Reference 3: Clin Orthop Rel Res 374, 201-11, 2000
Non-patent Reference 4: Arth & Reum 64, 1572-78, 2012
Non-patent Reference 5: J Arthroplasty 26, 1128-34, 2011
Non-patent Reference 6: Clin Orthop Rel Res 443, 273-79, 2006
Non-patent Reference 7: J Bone Joint Surg 87A, 2155-2159, 2005
Non-patent Reference 8: N Eng J Med 363, 2396-2405, 2010
Non-patent Reference 9: N Eng J Med 363, 2473-4, 2010
Non-patent Reference 10: J Orthop Sci 13, 533-42, 2008
Non-patent Reference 11: Bone 40, 1475-82, 2007
Non-patent Reference 12: Rheum Int 32, 1367-1370, 2012
Non-patent Reference 13: Clin Orthop Rel Res 305, 190-99, 1994
Non-patent Reference 14: J Bone Joint Surg Br 81, 590-595, 1999
Non-patent Reference 15: Hokkaido Journal of Orthopaedics and Traumatology, Vol. 125, 83, 2013
Non-patent Reference 16: Bone 42, S80, 2008
Non-patent Reference 17: Int. J. Oral Maxillofac. Surg. 42, 1475-1480, 2013
Non-patent Reference 18: Cacif Tissue Int 95, 94-96, 2014

SUMMARY OF THE INVENTION

Problems to be Solved by the Invention

The problem to be solved by the present invention is to provide an agent for preventing onset and/or suppressing progress of ION.

Means Used to Solve the Above-Mentioned Problems

As a result of in-depth studies intended to solve the above problem, the present inventors discovered that, surprisingly enough, intermittent administration of parathyroid hormone or a derivative thereof to ION patients, especially administration of 56.5 µg/time of parathyroid hormone or a derivative thereof once a week to ION patients, demonstrates an excellent therapeutic effect (onset preventing and/or progress suppressing effect).

A 20 µg daily formulation and a 56.5 µg once-a-week formulation are used in clinical practice as teriparatide formulations to treat osteoporosis. While the daily formulation markedly increases bone formation markers, the once-a-week formulation increases bone formation markers only slightly, suggesting the possibility that the action on bone formation is not necessarily adequate. Given this situation, it was quite unexpected that the 56.5 µg once-a-week formulation was effective in ION patients.

Specifically, the present invention includes the following.

[1] An agent for preventing the onset of idiopathic osteonecrosis of the femoral head and/or suppressing the progress of the same comprising parathyroid hormone or a derivative thereof as an active ingredient, characterized by being administered intermittently.

[2] The agent for preventing the onset of idiopathic osteonecrosis of the femoral head and/or suppressing the progress of the same according to [1] wherein 56.5 µg/time of parathyroid hormone or a derivative thereof is administered once a week.

[3] The agent for preventing the onset of idiopathic osteonecrosis of the femoral head and/or suppressing the progress of the same according to [1] or [2] wherein the parathyroid hormone or derivative thereof is human PTH (1-34).

[4] The agent for preventing the onset of idiopathic osteonecrosis of the femoral head and/or suppressing the progress of the same according to any of [1]-[3] wherein the parathyroid hormone or derivative thereof is teriparatide acetate.

[5] The agent for preventing the onset of idiopathic osteonecrosis of the femoral head and/or suppressing the progress of the same according to any of [1]-[4], the agent being administered to an idiopathic osteonecrosis of the femoral head patient in type A, B, C1, or C2.

[6] The agent for preventing the onset of idiopathic osteonecrosis of the femoral head and/or suppressing the progress of the same according to any of [1]-[5] for suppressing femoral head collapse.

[7] The agent for preventing the onset of idiopathic osteonecrosis of the femoral head and/or suppressing the progress of the same according to any of [1]-[6] that is a freeze-dried formulation for subcutaneous injection.

[8] The agent for preventing the onset of idiopathic osteonecrosis of the femoral head and/or suppressing the progress of the same according to any of [1]-[7], characterized in being administered over a period of 24 weeks or longer.

Advantages of the Invention

Administration of the agent for preventing onset of the present invention and/or suppressing the progress of the same can suppress onset and/or progress in ION patients. Previously, drug treatment by anti-inflammatory analgesics and lifestyle guidance were given when ION developed, and the treatment could not be called adequate. The present invention provides a new conservative treatment option for ION and so on.

BRIEF DESCRIPTION OF THE DRAWINGS

FIG. 1 shows the schedule of the Example 1 study. In the drawing, "Xp" means "evaluation of femoral head collapse and band like sclerosis by x-ray (bilateral hip joint frontal views and lateral hip joint views)." In FIG. 1, each patient was observed over the course of two years while teriparatide was administered once a week for 72 weeks, as a general rule, meaning that the imaging studies shown in FIG. 1 were performed at fixed times during that two years (four weeks, 12 weeks, 24 weeks, 36 weeks, one year, 72 weeks, and two years after the start of administration).

In FIG. 2, "weeks of survival" means the number of weeks elapsed from the start of administration until the time of observation (evaluation) in the Example 2 study. In the drawing, "discontinued" means that, at the time represented by the short vertical line, one subject each was dropped from the patients evaluated as subjects of Kaplan-Meyer analysis during observation.

MODE FOR CARRYING OUT THE INVENTION

The mode for carrying out the present invention is explained concretely below.

Active Ingredient

The parathyroid hormone (abbreviated hereinafter as "PTH") useful as the active ingredient for the agent for preventing onset and/or suppressing progress of the present invention encompasses any of natural PTH, PTH produced by genetic engineering techniques, PTH synthesized by chemical synthesis, or arbitrary mixtures thereof. PTH can be synthesized by genetic engineering techniques that are themselves known. Alternatively, PTH can be synthesized by peptide synthesis methods that are themselves known. For example, PTH can also be synthesized by a solid phase method whereby a peptide chain is extended from the C end on an in soluble polymer carrier. Furthermore, the origin of the PTH that is the active ingredient of the agent for preventing onset and/or suppressing progress of the present invention is not limited to human, but may be murine, bovine, porcine, or the like.

The agent for preventing onset and/or suppressing progress of the present invention can also comprise a PTH derivative as its active ingredient. Physiologically active PTH fragments can be given as examples of PTH derivatives. A physiologically active PTH fragment means a partial peptide of PTH, a peptide in which some of the amino acids of a partial peptide of PTH have been substituted by other amino acids, a peptide in which some of the amino acids of a partial peptide of PTH have been deleted, or a peptide in which one or more amino acids have been added to a partial peptide of PTH, wherein the peptide has the physiological activity (for example, serum calcium concentration elevating effect) of PTH.

Human PTH (1-34) can be given as a preferred example of a physiologically active PTH fragment. In this specification, human PTH (n-m) means a peptide shown by a partial amino acid sequence consisting of from number n to number m of the amino acid sequence of human PTH (1-84). For example, human PTH (1-34) means a peptide shown by a partial amino acid sequence from number 1 to number 34 of the amino acid sequence of human PTH (1-84). Human PTH (1-84) or human PTH (1-34) can be given as preferred examples of the PTH or PTH derivative that is the active ingredient of the agent for preventing onset and/or suppressing progress of the present invention. Human PTH (1-34) can be given as the most preferred example. Human PTH (1-34) can be produced by a known method.

The PTH or PTH derivative that is the active ingredient of the agent for preventing onset and/or suppressing progress of the present invention may be a salt of one or more organic acids. Volatile organic acids are preferably used as the organic acid. Examples of volatile organic acids include trifluoroacetic acid, formic acid, acetic acid, and the like. Acetic acid is a preferred example. The ratio of the two when forming a salt from free PTH or PTH derivative and an organic acid is not particularly restricted as long as a salt can be formed. For example, since human PTH (1-34) has nine molecules of basic amino acid residues and four molecules of acidic amino acid residues in its molecule, five basic amino acid residues can be taken as the chemical equivalent of acetic acid, taking into consideration salt formation within these molecules. For example, as a theory, if an acetic acid content represented by acetic acid weight×100(%)/peptide weight of human PTH (1-34) is used as the amount of acetic acid, the chemical equivalent of acetic acid to human PTH (1-34), which is in a free form, becomes approximately 7.3% (wt. %).

In this specification, human PTH (1-34), which is in a free form, is sometimes referred to as teriparatide, and the acetate of teriparatide is referred to as teriparatide acetate. The acetic acid content in teriparatide acetate is not particularly restricted as long as the teriparatide and acetic acid form a salt. For example, it may be 7.3%, which is the theoretical chemical equivalent mentioned above, or higher, or may be 0-1%. More specifically, examples of the acetic acid content in teriparatide acetate include 1-7%, preferably 2-6%. These salts can be produced by methods that are themselves known. Teriparatide acetate can be given as a preferred example of the active ingredient of the agent for preventing onset and/or suppressing progress of the present invention.

Indications and Preventing Onset and/or Suppressing Progress Thereof

The agent for preventing onset and/or suppressing progress of the present invention can be used as an agent for preventing the onset and/or suppressing the progress of idiopathic osteonecrosis of the femoral head (ION). Idiopathic osteonecrosis of the femoral head means that part of the femoral head has fallen into a state of necrosis, related to steroid administration, excessive alcohol intake, and the like.

Idiopathic osteonecrosis of the femoral head can be categorized by risk factor as steroidal or alcoholic, or idiopathic in the narrow sense that there is no clear risk factor.

The presence or absence of the development of idiopathic osteonecrosis can be assessed by known diagnostic criteria. For example, a confirmed diagnosis can be made if two or more of the following five criteria are met (except tumors, tumorous conditions, and epiphyseal dysplasia). (1) and (2) are both x-ray findings and can be judged from simple x-ray images of hip joint frontal views or lateral views. (3), (4), and (5) are all test findings.

(1) Femoral head collapse or subchondral fracture of the femoral head (crescent sign) by simple x-ray (2) Formation of band like sclerosis in the femoral head by simple x-ray (3) Cold in hot image of the femoral head by bone scintigraphy (4) Band image in femoral head in MRI T1-enhanced image (5) Bone necrosis image with repair reaction layer in bone biopsy specimen Idiopathic osteonecrosis of the femoral head can also be classified by stage of disease (Stage). In Stage 1, there are no abnormal findings by simple x-ray, but there are abnormal findings by MRI, bone scintigraphy, and histopathological images. In Stage 2, band like sclerosis are found by simple x-ray, but there is no collapse of the femoral head. In Stage 3, there is collapse of the femoral head, but the joint space is maintained. Stage 3 is further classified by the extent of collapse; collapse of less than 3 mm is 3A and 3 mm or greater is 3B. In Stage 4, osteoarthritic changes appear. Stages 1, 2, 3 (3A and 3B), and 4 are also sometimes referred to as disease stages 1, 2, 3 (3A and 3B), and 4.

Generally in idiopathic osteonecrosis of the femoral head, the point at which part of the femoral head falls into necrosis is called "occurrence," as differentiated from symptom and femoral head collapse which is called "onset." Preventing onset in the present invention means preventing or suppressing the onset of symptoms of idiopathic osteonecrosis of the femoral head or femoral head collapse. Suppressing progress in the present invention means preventing or suppressing progress of the symptoms of idiopathic osteonecrosis of the femoral head or femoral head collapse that have occurred.

Idiopathic osteonecrosis of the femoral head can also be classified by disease type (Type). Type A is a type in which the necrotic zone is less than $\frac{1}{3}$ of the inside of the acetabular load surface or the necrotic zone is present only in a non-load portion. Type B is a type in which the necrotic zone is from $\frac{1}{3}$ to less than $\frac{2}{3}$ of the inside of the acetabular load surface. Type C is a type in which the necrotic zone extends to $\frac{2}{3}$ or more of the inside of the acetabular load surface. Type C can be further categorized as Type C-1 and Type C-2. Type C-1 is a type in which the outer edge of the necrotic zone is within the acetabular margins; Type C-2 is a type in which the outer edge of the necrotic zone exceeds the acetabular margins. The disease type allows one to predict to a certain extent the future probability of the occurrence of pain (or femoral head collapse rate). Patients categorized as Type C in particular (Especially Type C-2) have a high probability of femoral head collapse. Type A, Type B, and Type C (type C-1 and type C-2) are also sometimes respectively referred to as disease types A, B, and C (C1 and C2).

In Example 1 of this application, the agent for preventing onset and/or suppressing progress of the present invention was shown to be effective even in idiopathic osteonecrosis of the femoral head patients of Type C1 or C2 who have a large necrotic region and are at high risk of femoral head collapse. The agent for preventing onset and/or suppressing progress of the present invention therefore can be applied to idiopathic osteonecrosis of the femoral head patients of not only Types A and B, but also those of Types C1 and C2.

On the other hand, the agent for preventing onset and/or suppressing progress of the present invention is preferably not applied to the patients of idiopathic osteonecrosis of the femoral head (1) for whom administration of teriparatide or teriparatide acetate is contraindicated, (2) who have already undergone total hip arthroplasty (THA) or bipolar hip arthroplasty (BHA), (3) who have serious renal dysfunction, hepatic dysfunction, or cardiac dysfunction, (4) who have osteoarthritic changes to the hip joint on the affected side, and the like.

The preventative effect on onset and/or suppressive effect on progress in the present invention can be confirmed by the physician using evaluation of femoral head collapse by simple x-ray (bilateral hip joint frontal views and two-direction hip joint side views), evaluation of the femoral head necrotic zone by MRI, or clinical evaluation (VAS pain score, Japan Orthopedic Society score, Harris hip score, or the like).

Dosage and Administration

One characteristic of the agent for preventing onset and/or suppressing progress of the present invention is that it is administered intermittently. Preferably, the agent for preventing onset and/or suppressing progress of the present invention can be provided as a formulation to administer 56.5 μg/time of PTH or a PTH derivative at a frequency of once a week to an idiopathic osteonecrosis of the femoral head patient.

Here, "administration of 56.5 μg/time of PTH or a PTH derivative" means "administration of 56.5 μg/time of PTH or a PTH derivative as the amount equivalent to the free compound." For example, when the PTH or PTH derivative is teriparatide acetate, this becomes "administration of 56.5 μg/time of teriparatide acetate as the amount equivalent to teriparatide." When the agent for preventing onset and/or suppressing progress of the present invention is made into a freeze-dried formulation for dissolution at the time of use (such as a vial formulation) or solution (such as a prefilled injection) and the agent is administered to a patient, some residual solution can adhere to the container. Therefore, the content of PTH or PTH derivative comprised in the agent must be adjusted taking into consideration the residual solution when preparing a specific agent; one skilled in the art can make this adjustment easily by a customary method. For example, when the PTH or PTH derivative is teriparatide acetate and the agent for preventing onset and/or suppressing progress of the present invention is made into a freeze-dried vial formulation for dissolution at the time of use, the vial can contain 67.9 μg of teriparatide acetate (63.3 μg as teriparatide).

The route of administration of the agent for preventing onset and/or suppressing progress of the present invention is not particularly restricted, but subcutaneous administration is preferred.

The duration of administration of the agent for preventing onset and/or suppressing progress of the present invention is not particularly restricted, but is preferably 24 weeks or longer, more preferably 48 weeks or longer, and even more preferably up to 96 weeks.

The agent for preventing onset and/or suppressing progress of the present invention can be administered in combination with other agents. For example, it can be used in combination with other effective bisphosphonate formulations (alendronate and the like). Anti-inflammatory analgesics can be used in combination when an idiopathic osteonecrosis of the femoral head patient being administered the agent for preventing onset and/or suppressing progress of the present invention complains of pain due to femoral head collapse. Steroids and the like can also be continued without modification and used in combination as necessary when the agent for preventing onset and/or suppressing progress of the present invention is used in steroid induced osteonecrosis of the femoral head that has developed when utilizing high-dose steroids for treatment of a collagen disease such as systemic lupus erythematosus (SLE). Alternatively, the agent for preventing onset and/or suppressing progress of the present invention can also be used in combination with at least one compound selected from the group consisting of calcium, vitamin D, and magnesium.

The agent for preventing onset and/or suppressing progress of the present invention is preferably administered as a conservative treatment prior to applying surgical treatment. Nonetheless, it can also be administered for the purpose of suppressing the progress of femoral head collapse or the like after femoral varus osteotomy or transtrochanteric rotational osteotomy.

Formulation

The dosage form of the agent for preventing onset and/or suppressing progress of the present invention is not particularly restricted. For example, it may be a solution or a freeze-dried formulation that can be used by dissolution in a suitable solvent such as physiological saline solution at the time of use. The agent for preventing onset and/or suppressing progress of the present invention is preferably a freeze-dried formulation for subcutaneous injection. The agent for preventing onset and/or suppressing progress of the present invention can also comprise necessary additives (for example, excipients, stabilizers, dissolution auxiliaries, antioxidants, pain relievers, isotonifying agents, pH adjusters, preservatives, and the like) in addition to the PTH or PTH derivative. Examples of such additives include sugars, amino acids, salt, and the like. When sugars are used as an additive, mannitol, glucose, sorbitol, inositol, sucrose, maltose, lactose, or trehalose is preferably added in a quantity of 1 part by weight or more (preferably 50-1000 parts by weight) per 1 part by weight of PTH. When sugars and salt are used as additives, $1/1000$-$1/5$ part by weight (preferably $1/100$-$1/10$ part by weight) of salt is preferred per 1 part by weight of sugars.

EXAMPLES

The present invention is explained more concretely below through examples. The present invention, however, is not limited to these examples.

Example 1

Clinical Research on Parathyroid Hormone Formulation in Idiopathic Osteonecrosis of the Femoral Head 1. Materials and Methods A randomized two-group comparative study was conducted by dividing patients to whom the purpose and utility of the study had been explained and who had consented to participate in the study into two groups: a PTH administered group and a control group (non-PTH administered group). Furthermore, the patients were assigned basically using a minimization method of the assignment factors (age, sex, cause of ION, disease type). Each patient in the PTH administered group was subcutaneously administered a PTH formulation (Teribone 56.5 μg for subcutaneous injection (manufactured by Asahi Kasei Pharma); sometimes simply referred to as Teribone; the active ingredient of this formulation is teriparatide acetate) at a frequency of once a week in a dose of 56.5 μg as teriparatide. The patients of both the PTH administered group and non-PTH administered group were orally administered a calcium, vitamin D, magnesium formulation as a basic drug. The duration of administration and the observation period were set at 72 weeks and 2 years, respectively, from the time of the first administration of the formulation. Evaluation was performed by the following image inspections.

(1) Image Evaluation (1) Evaluation of femoral head collapse by x-ray (bilateral hip joint frontal views, lateral hip joint views) (Non-patent Document 14).

Figure 1:
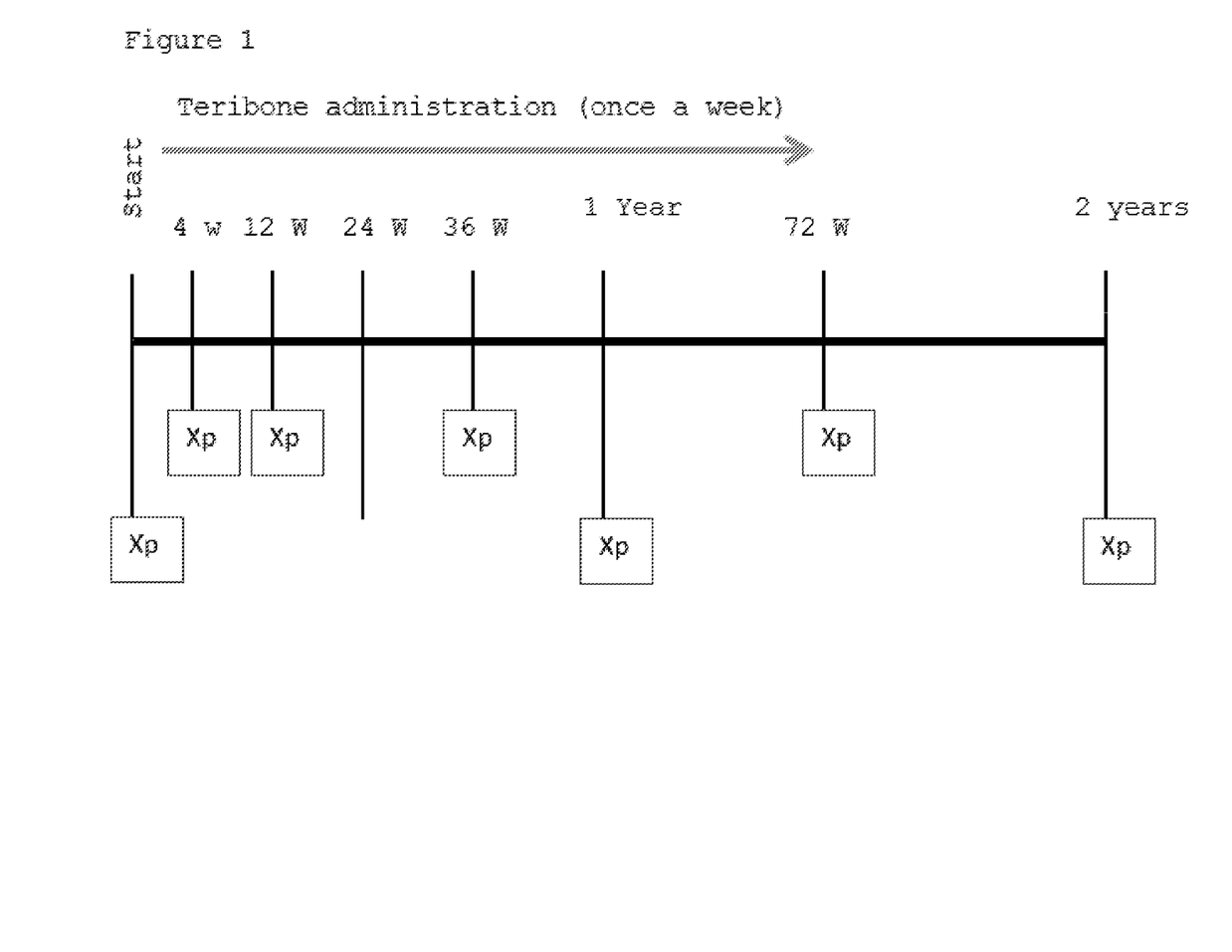

FIG. 1 shows the study schedule.

Enrolled as of Jan. 15, 2015 are 28 hips (18 persons); 12 hips (9 persons) in the PTH administered group and 16 hips (9 persons) in the non-PTH administered group (Table 1).

TABLE 1

Patient background

| N | PTH group 12 hips (9 persons) | Control group 16 hips (9 persons) | p |
|---|---|---|---|
| Sex (male/female) | 6/3 | 5/4 | 1.00 |
| Average age (years) | 52.7 (29-66) | 43.8 (17-72) | 0.273 |
| Right or left (right/left) (hip) | 9/3 | 8/8 | 0.253 |
| Cause (steroid/alcohol/idiopathic) (persons) | 5/3/1 | 5/3/1 | 1.00 |
| Type (A/B/C1/C2) (hip) | 0/0/2/10 | 0/2/8/6 | 0.030* |
| Stage at start (1/2/3A/3B) (hip) | 5/1/6/0 | 7/6/3/0 | 0.110 |

*More C2 in PTH group

The disease type was significantly greater in the PTH group (p=0.030, Table 1). This is understood to be an effect of many both side cases in the control group, and low disease types in one side cases.

2. Results

The changes in disease stage are shown in comparison to at the start based on x-rays taken after 24 weeks and 48 weeks (shown as one year in the study schedule of FIG. 1) (Tables 2 and 3).

TABLE 2

Disease stage at 24 weeks

| | | Worse | Not worse | Total |
|---|---|---|---|---|
| PTH group | Frequency | 4 | 8 | 12 |
| | Adjusted residual difference | −1.2 | 1.2 | |
| Control group | Frequency | 9 | 7 | 16 |
| | Adjusted residual difference | 1.2 | −1.2 | |
| Total | Frequency | 13 | 15 | 28 | p = 0.229

TABLE 3

Disease stage at 48 weeks

| | | Worse | Not worse | Total |
|---|---|---|---|---|
| PTH group | Frequency | 5 | 5 | 10 |
| | Adjusted residual difference | −1.5 | 1.5 | |
| Control group | Frequency | 9 | 2 | 11 |
| | Adjusted residual difference | 1.5 | −1.5 | |
| Total | Frequency | 14 | 7 | 21 | p = 0.183

The time until femoral head collapse in the PTH group was 8.0 months on average in contrast to 4.0 months on average in the control group. When femoral head collapse occurred, the time tended to be shorter in the control group than in the PTH group (p=0.081).

Looking at changes in stage up to the present, the stage progressed in 6 of 12 hips in the PTH group. Progress in stage was seen in 11 of 16 hips in the control group (Table 4).

TABLE 4

Changes in all latest x-rays, including cases just started

| | | Worse | Not worse | Total |
|---|---|---|---|---|
| PTH group | Frequency | 6 | 6 | 12 |
| | Adjusted residual difference | −1.0 | 1.0 | |
| Control group | Frequency | 11 | 5 | 16 |
| | Adjusted residual difference | 1.0 | −1.0 | |
| Total | Frequency | 17 | 11 | 28 | p = 0.441

Looking at Type C in which the necrotic zone is large and the risk of femoral head collapse is high, no progress in stage was seen in 4 of 10 hips of C2 or in 2 of 2 hips of C1 in the PTH group. In the control group, progress in stage was seen in all 6 hips in C2 and in 5 of 8 hips in C1.

The femoral head collapse rate tended to be less than that in the control group in the PTH group, which included a significantly larger number of cases of high disease type (24 weeks: 33% vs. 56%; 48 weeks: 50% vs. 82%; to present: 50% vs. 69%).

Incidentally, the femoral head collapse rate was calculated based on Tables 2 and 3. For example, the femoral head collapse rate of the PTH group 24 weeks after the start of administration (24 weeks: 33%) was calculated as 4/12×100 (%).

In addition, while femoral head collapse progressed in all cases (6/6 hips) in C2, in which the necrotic region is large, in the control group, femoral head collapse progress was not seen in less than half (4/10 hips) even in C2 in the PTH group. In C1, while femoral head collapse progressed in 5 of 8 hips in the control group, femoral head collapse was not seen in 2 of 2 hips in the PTH group.

The present inventors believe that the above results suggest the possibility that the use of PTH reduces the femoral head collapse rate, although it cannot prevent femoral head collapse in all cases, and, if we look at Type C in which the necrotic zone is large and the risk of femoral head collapse is high, the possibility that femoral head collapse can be greatly reduced in C1, and the possibility of reduction even in C2 was suggested.

Example 2

Clinical Research on Parathyroid Hormone Formulation in Idiopathic Osteonecrosis of the Femoral Head The materials and method of this study were essentially the same as the materials and method of the clinical research described in Example 1, except for the number of patients and the observation period. This study is not a study conducted independently of the clinical research described in Example 1, but a study that continued evaluation carried out during the clinical research described in Example 1 with newly enrolled patients added during the extended period.

(Number of patients) Enrolled as of May 8, 2016 are 32 hips (21 persons); 13 hips (10 persons) in the PTH administered group and 19 hips (11 persons) in the non-PTH administered group (Table 5).

TABLE 5

Patient background

| N | PTH group 13 hips (10 persons) | Control group 19 hips (11 persons) | p |
|---|---|---|---|
| Sex (male/female) | 7/3 | 7/4 | 1.000 |
| Average age (years) | 52.0 (29-66) | 47.0 (17-72) | 0.482 |
| Right or left (right/left) (hip) | 10/3 | 10/9 | 0.153 |
| Cause (steroid/alcohol/idiopathic) (persons) | 5/4/1 | 7/3/1 | 0.817 |
| Type (A/B/C1/C2) (hip) | 0/0/3/10 | 0/2/8/9 | 0.259 |
| Stage at start (1/2/3A/3B) (hip) | 5/1/7/0 | 9/6/4/0 | 0.110 |

No significant differences were found between the PTH group and the control group in sex, age, right or left, cause, Type, or stage at the start.

2. Results

Changes in the stage by x-ray at 4, 12, 24, 48, 72, and 96 weeks from the start of administration in comparison to the stage at start are shown below (Tables 6-11).

TABLE 6

Groups and 4 week cross table

| | | | 4 weeks | | |
|---|---|---|---|---|---|
| | | | Worse | Not worse | Total |
| Group | PTH | Frequency | 0 | 13 | 13 |
| | | Adjusted residual difference | −1.5 | 1.5 | |
| | Control | Frequency | 3 | 16 | 19 |
| | | Adjusted residual difference | 1.5 | −1.5 | |
| Total | | Frequency | 3 | 29 | 32 | p = 0.195

TABLE 7

Groups and 12 week cross table

| | | | 12 weeks | | |
|---|---|---|---|---|---|
| | | | Worse | Not worse | Total |
| Group | PTH | Frequency | 2 | 11 | 13 |
| | | Adjusted residual difference | −1.9 | 1.9 | |
| | Control | Frequency | 9 | 10 | 19 |
| | | Adjusted residual difference | 1.9 | −1.9 | |
| Total | | Frequency | 11 | 21 | 32 | p = 0.066

TABLE 8

Groups and 24 week cross table

| | | | 24 weeks | | |
|---|---|---|---|---|---|
| | | | Worse | Not worse | Total |
| Group | PTH | Frequency | 4 | 9 | 13 |
| | | Adjusted residual difference | −1.5 | 1.5 | |
| | Control | Frequency | 11 | 8 | 19 |
| | | Adjusted residual difference | 1.5 | −1.5 | |
| Total | | Frequency | 15 | 17 | 32 | p = 0.131

TABLE 9

Groups and 48 week cross table

| | | | 48 weeks | | |
|---|---|---|---|---|---|
| | | | Worse | Not worse | Total |
| Group | PTH | Frequency | 5 | 7 | 12 |
| | | Adjusted residual difference | −1.5 | 1.5 | |
| | Control | Frequency | 13 | 6 | 19 |
| | | Adjusted residual difference | 1.5 | −1.5 | |
| Total | | Frequency | 18 | 13 | 31 | p = 0.141

TABLE 10

Groups and 72 week cross table

| | | | 72 weeks | | |
|---|---|---|---|---|---|
| | | | Worse | Not worse | Total |
| Group | PTH | Frequency | 6 | 6 | 12 |
| | | Adjusted residual difference | −1.5 | 1.5 | |
| | Control | Frequency | 13 | 4 | 17 |
| | | Adjusted residual difference | 1.5 | −1.5 | |
| Total | | Frequency | 19 | 10 | 29 | p = 0.140

TABLE 11

Groups and 96 week cross table

| | | | 96 weeks | | |
|---|---|---|---|---|---|
| | | | Worse | Not worse | Total |
| Group | PTH | Frequency | 6 | 6 | 12 |
| | | Adjusted residual difference | −2.2 | 2.2 | |
| | Control | Frequency | 14 | 2 | 16 |
| | | Adjusted residual difference | 2.2 | −2.2 | |
| Total | | Frequency | 20 | 8 | 28 | p = 0.040

Looking at the changes in disease stage at each time point, a tendency for the progress in stage to be less in the PTH group than in the control group was seen at 4, 12, 24, 48, and 72 weeks, and a significant difference was found at 96 weeks (p=0.040).

Looking at Type C in which the necrotic region is large and the risk of femoral head collapse is high, progress in disease stage was not seen in 4 of 10 hips in C2 and in 4 of 4 hips in C1 in the PTH group. The stage progressed in 8 of 9 hips in C2 and in 5 of 8 hips in C1 in the control group.

Looking at the changes in stage to date, progress in stage was seen in 6 of 13 hips in the PTH group. Progress in stage was seen in 14 of 19 hips in the control group (Table 12).

TABLE 12

Groups and final cross table

| | | | Final | | |
|---|---|---|---|---|---|
| | | | Worse | Not worse | Total |
| Group | PTH | Frequency | 6 | 7 | 13 |
| | | Adjusted residual difference | −1.6 | 1.6 | |
| | Control | Frequency | 14 | 5 | 19 |
| | | Adjusted residual difference | 1.6 | −1.6 | |
| Total | | Frequency | 20 | 12 | 32 | p = 0.114

Figure 2:
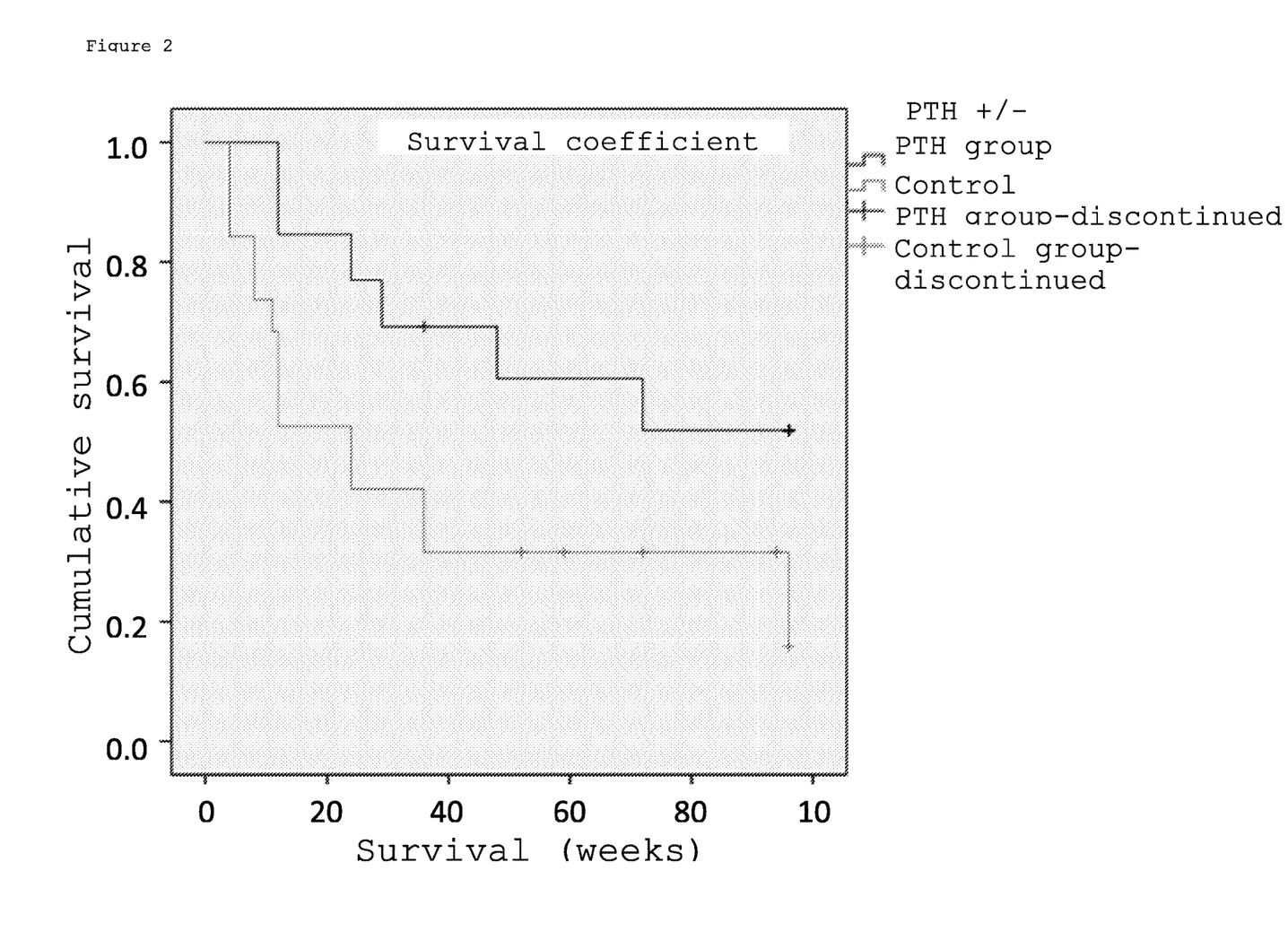
FIG. 2 is the Kaplan-Meier survival curves of the PTH group and control group in the Example 2 study, taking as the endpoint when collapse of the femoral head progressed (stage progress) on the x-ray or surgery was performed.

A Kaplan-Meyer survival curve is shown, taking femoral head collapse progress (stage progress) on the x-ray or surgery as the endpoint in the PTH group and the control group (FIG. 2, Table 13).

TABLE 13

Overall comparison

| | $\chi^2$ | Degree of freedom | p value |
|---|---|---|---|
| Log rank (Mantel-Cox) | 3.991 | 1 | 0.046 |

As a result of a log rank test of the Kaplan-Meyer survival curve, when collapse progress (stage progress) or performance of surgery was taken as the endpoint, a tendency was seen for collapse progress (change in stage) or surgery to be suppressed in the PTH group from soon after the start of administration, and a statistically significant difference was found (p=0.046) between the PTH group and the control group.

INDUSTRIAL APPLICABILITY

The present invention is useful for preventing the onset of idiopathic osteonecrosis of the femoral head and/or suppressing the progress of the same and provides a new conservative treatment for idiopathic osteonecrosis of the femoral head patients.

The invention claimed is:

1. A method for treating idiopathic osteonecrosis of the femoral head and/or suppressing the progress of the same in a patient in need thereof, comprising:
    administering intermittently to the patient an effective amount of an agent comprising parathyroid hormone or a derivative thereof as an active ingredient,
    wherein 56.5 μg/time of said parathyroid hormone or derivative thereof is administered once a week.

2. The method according to claim 1, wherein the parathyroid hormone or derivative thereof is human PTH (1-34).

3. The method according to claim 1, wherein the parathyroid hormone or derivative thereof is teriparatide acetate.

4. The method according to claim 1, wherein said agent is administered to an idiopathic osteonecrosis of the femoral head in a patient having disease type A, B, C1, or C2.

5. The method according to claim 1, wherein said agent is administered to an idiopathic osteonecrosis of the femoral head in a patient having disease type C1 or C2.

6. The method according to claim 1, wherein said agent is a freeze-dried formulation that is dissolved at a time of use and is administered by subcutaneous injection.

7. The method according to claim 1, wherein said agent is administered over a period of 24 weeks or longer.

8. A method for suppressing femoral head collapse in a patient having idiopathic osteonecrosis of the femoral head, comprising:
    administering intermittently to the patient an effective amount of an agent comprising parathyroid hormone or a derivative thereof as an active ingredient,
    wherein 56.5 μg/time of said parathyroid hormone or derivative thereof is administered once a week.

9. The method according to claim 6, wherein said agent is administered to an idiopathic osteonecrosis of the femoral head in a patient having disease type C1 or C2.

* * * * *